US010299038B2

(12) United States Patent
Kim et al.

(10) Patent No.: US 10,299,038 B2
(45) Date of Patent: *May 21, 2019

(54) CAPTURING WIDE-BAND AUDIO USING MICROPHONE ARRAYS AND PASSIVE DIRECTIONAL ACOUSTIC ELEMENTS

(71) Applicant: Bose Corporation, Framingham, MA (US)

(72) Inventors: Wontak Kim, Cambridge, MA (US); Austin Mackey, Brighton, MA (US); Joseph A. Coffey, Jr., Hudson, MA (US)

(73) Assignee: Bose Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,464

(22) Filed: Aug. 21, 2018

(65) Prior Publication Data

US 2018/0359565 A1 Dec. 13, 2018

Related U.S. Application Data

(63) Continuation of application No. 15/406,045, filed on Jan. 13, 2017, now Pat. No. 10,097,920.

(51) Int. Cl.
*H04R 3/00* (2006.01)
*H03G 7/00* (2006.01)
(Continued)

(52) U.S. Cl.
CPC ........... *H04R 3/005* (2013.01); *H04R 1/2876* (2013.01); *H04R 1/326* (2013.01); *H04R 1/406* (2013.01); *G10L 2021/02166* (2013.01); *H04R 1/086* (2013.01); *H04R 1/2807* (2013.01); *H04R 1/342* (2013.01); *H04R 1/40* (2013.01); *H04R 5/027* (2013.01); *H04R 9/08* (2013.01); *H04R 17/00* (2013.01); *H04R 2201/401* (2013.01); *H04R 2201/403* (2013.01); *H04R 2430/21* (2013.01);
(Continued)

(58) Field of Classification Search
CPC ........ H04R 3/005; H04R 1/04; H04R 19/016; H04R 1/2876; H04R 1/326; H04R 1/406; H04R 5/027; H04R 17/00; H04R 2201/401; H04R 2430/21
USPC ................ 381/92, 102; 600/439, 463; 601/2
See application file for complete search history.

(56) References Cited

U.S. PATENT DOCUMENTS 6,084,973 A * 7/2000 Green .................... H04R 3/005 381/92
6,321,428 B1 * 11/2001 Toda .................... B06B 1/0688 29/25.35

(Continued)

*Primary Examiner* — Paul Kim
*Assistant Examiner* — Ubachukwu A Odunukwe
(74) *Attorney, Agent, or Firm* — Fish & Richardson P.C.

(57) ABSTRACT

The technology described in this document can be embodied in an apparatus that includes an array of multiple microphones, and a passive directional acoustic element disposed between at least two of the multiple microphones. The passive directional acoustic element includes a pipe having an elongated opening along at least a portion of the length of the pipe, and an acoustically resistive material covering at least a portion of the elongated opening. One or more structural characteristics of the passive acoustic element is configured for capturing a target frequency range in accordance with a target beam pattern associated with the array.

25 Claims, 7 Drawing Sheets

(51) Int. Cl.

| | |
|---|---|
| ***A61B 8/12*** | (2006.01) |
| ***A61N 7/00*** | (2006.01) |
| ***H04R 1/32*** | (2006.01) |
| ***H04R 1/28*** | (2006.01) |
| ***H04R 1/40*** | (2006.01) |
| *H04R 1/34* | (2006.01) |
| *H04R 17/00* | (2006.01) |
| *H04R 5/027* | (2006.01) |
| *G10L 21/0216* | (2013.01) |
| *H04R 1/08* | (2006.01) |
| *H04R 9/08* | (2006.01) |

(52) U.S. Cl.
CPC ...... *H04R 2430/23* (2013.01); *H04R 2499/11* (2013.01)

(56) References Cited

U.S. PATENT DOCUMENTS

| | | | | |
|---|---|---|---|---|
| 8,351,630 | B2 | 1/2013 | Ickler et al. | |
| 8,358,798 | B2 | 1/2013 | Ickler et al. | |
| 8,447,055 | B2 | 5/2013 | Jankovsky et al. | |
| 2006/0126865 | A1* | 6/2006 | Blamey | H03G 3/32 381/102 |
| 2009/0310811 | A1 | 12/2009 | Inoda et al. | |
| 2010/0098266 | A1* | 4/2010 | Mukund | G10L 21/0208 381/94.7 |
| 2012/0275621 | A1* | 11/2012 | Elko | H04R 19/016 381/92 |
| 2013/0287225 | A1* | 10/2013 | Niwa | H04R 3/00 381/92 |
| 2016/0161588 | A1* | 6/2016 | Benattar | H04R 3/005 367/119 |
| 2016/0353201 | A1* | 12/2016 | Akino | H04R 1/342 |

* cited by examiner

CAPTURING WIDE-BAND AUDIO USING MICROPHONE ARRAYS AND PASSIVE DIRECTIONAL ACOUSTIC ELEMENTS

CLAIM OF PRIORITY

This application is a continuation application to U.S. patent application Ser. No. 15/406,045, filed on Jan. 13, 2017, the entire contents of which are hereby incorporated by reference.

TECHNICAL FIELD

This disclosure generally relates to acoustic devices that include microphone arrays for capturing acoustic signals.

BACKGROUND

An array of microphones can be used for capturing acoustic signals along a particular direction.

SUMMARY

In general, in one aspect, this document features an apparatus that includes an array of multiple microphones, and a passive directional acoustic element disposed between at least two of the multiple microphones. The passive directional acoustic element includes a pipe having an elongated opening along at least a portion of the length of the pipe, and an acoustically resistive material covering at least a portion of the elongated opening. One or more structural characteristics of the passive acoustic element is configured for capturing a target frequency range in accordance with a target beam pattern associated with the array.

In another aspect, this document features a device that includes one or more acoustic transducers, an array of multiple microphones, and a passive directional acoustic element disposed between at least two of the multiple microphones. The passive directional acoustic element includes a pipe having an elongated opening along at least a portion of the length of the pipe, and an acoustically resistive material covering at least a portion of the elongated opening. One or more structural characteristics of the passive acoustic element is configured for capturing a target frequency range in accordance with a target beam pattern associated with the array, the target beam-pattern being selected in accordance with a threshold amount of spatial aliasing. The device also includes one or more processing devices configured to process signals captured by the array.

In another aspect, this document features a method that includes receiving an input signal from an array of multiple microphones, wherein the input signal includes acoustic signals received through a passive directional acoustic element disposed between at least two of the multiple microphones. The passive directional acoustic element includes a pipe having an elongated opening along at least a portion of the length of the pipe, and an acoustically resistive material covering at least a portion of the elongated opening. The method also includes generating, by one or more processing devices from the input signal, a beamformed signal that represents signals captured by the array in accordance with one or more directional sensitivity patterns of the array, and generating an output signal based on the beamformed signal.

In another aspect, the document features one or more machine-readable storage devices having encoded thereon computer readable instructions for causing one or more processing devices to perform various operations. The operations include receiving an input signal from an array of multiple microphones, wherein the input signal includes acoustic signals received through a passive directional acoustic element disposed between at least two of the multiple microphones. The passive directional acoustic element includes a pipe having an elongated opening along at least a portion of the length of the pipe, and an acoustically resistive material covering at least a portion of the elongated opening. The operations also include generating a beamformed signal that represents signals captured by the array in accordance with one or more directional sensitivity patterns of the array, and generating an output signal based on the beamformed signal.

Implementations of the above aspects may include one or more of the following features. The array can be a linear array or a non-linear array. The multiple microphones can be disposed around the periphery of an acoustic device. The pipe can have a substantially uniform hollow cross-section along its length. The acoustically resistive material can include at least one of: wire mesh, sintered plastic, or fabric. The array can include six or more microphones separated by passive directional acoustic elements. The array of multiple microphones can be disposed along a substantially circular path, and the passive directional acoustic element disposed between at least two of the multiple microphones can have a curved shape. The array of multiple microphones can be disposed on a top surface or sidewall of the apparatus. The target beam-pattern can be selected in accordance with a threshold amount of spatial aliasing. The target frequency range can have a bandwidth substantially equal to 20 KHz.

Various implementations described herein may provide one or more of the following advantages. By using passive directional acoustic elements together with microphones, wideband acoustic signals (e.g., over a bandwidth of 20 KHz) can be captured with high fidelity. For example, on one hand, the use of passive directional acoustic elements may allow for significantly mitigating effects of spatial aliasing on the captured signals without using a large number of microphones. On the other hand, by using a limited number of discrete microphones in an array, the resultant sensitivity pattern of the array may be prevented from becoming overly directional. Therefore, in some cases, using multiple microphones in combination with one or more passive directional acoustic elements may allow for implementing arrays that are sensitive over a large bandwidth without being overly directional. Such arrays may be useful, for example, in small form factor devices usable for recording high-fidelity audio such as that captured or recorded for virtual reality (VR) applications.

Two or more of the features described in this disclosure, including those described in this summary section, may be combined to form implementations not specifically described herein.

The details of one or more implementations are set forth in the accompanying drawings and the description below. Other features, objects, and advantages will be apparent from the description and drawings, and from the claims.

DETAILED DESCRIPTION

This document describes technology in which multiple microphones are employed with passive directional acoustic elements in capturing acoustic signals over a wide bandwidth and with a target amount of directionality. For example, a circular array of six microphones, with passive directional acoustic elements disposed between each pair of microphones, may be used to capture signals in a bandwidth of up to 20 KHz. In the absence of the passive directional acoustic elements, the spacing between the microphones needed for capturing such a bandwidth without substantial spatial aliasing would be very small (e.g., in the order of a fraction of a centimeter), which typically would lead to a requirement of a large number of microphones that may not be practically feasible in many applications. On the other hand, in some cases, the directionality associated with the passive acoustic elements may be too high for some practical applications. The technology described herein can be used for obtaining a combination of microphones and passive directional acoustic elements that yields a target sensitivity pattern (e.g., with a target amount of directionality) over a large bandwidth. This can be used, for example, to implement wideband arrays using a small number of microphones. Such arrays may be implemented on small form-factor devices (e.g., personal acoustic devices or small VR cameras) to capture high fidelity audio over large bandwidths.

Figure 1A:
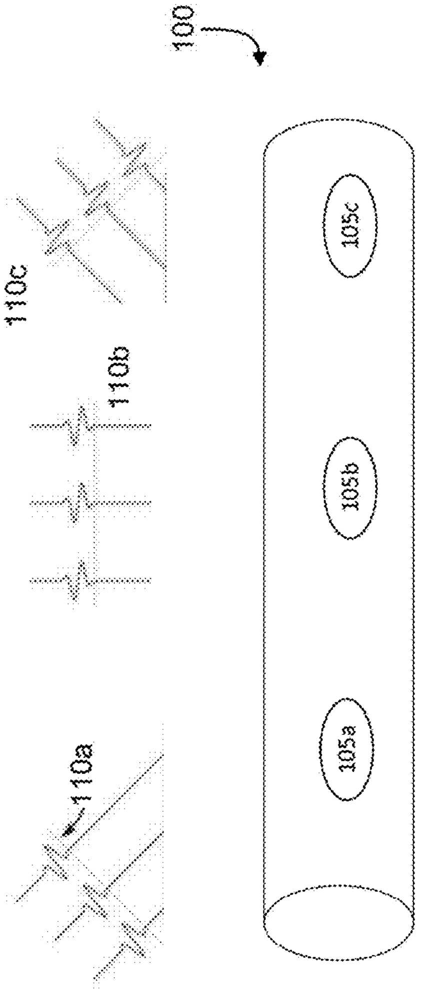
FIG. 1A is an example of a device with multiple microphones.

Microphone arrays can be used for capturing acoustic signals along a particular direction. For example, signals captured by multiple microphones in an array may be processed to generate a sensitivity pattern that emphasizes the signals along a "beam" in the particular direction and suppresses signals from one or more other directions. An example of such a device 100 is shown in FIG. 1. The device 100 includes multiple microphones 105 separated from one another by particular distances. The beamforming effect can be achieved by such an array of microphones. As illustrated in FIG. 1, the direction from which a wavefront 110*a*, 110*b* or 110*c* (110, in general) originates can have an effect on the time at which the wavefront 110 meets each microphone 105 in the array. For example, a wavefront 110*a* arriving from the left at a 45° angle to the microphone array reaches the left hand microphone 105*a* first, and then the microphones 105*b* and 105*c*, in that order. Similarly, a wavefront 110*b* arriving at an angle perpendicular to the array reaches each microphone 105 at the same time, and a wavefront 110*c* arriving from the right at an angle of 45° to the microphone array reaches the right microphone 105*c* first, and then the microphones 105*b* and 105*a*, in that order. If an output of the microphone array is calculated, for example, by summing the signals, signals originating from a source located perpendicular to the array will arrive at the microphones 105 at the same time, and therefore reinforce each other. On the other hand, signals originating from a non-perpendicular direction arrive at the different microphones 105 at different times and therefore results in a lower output amplitude. The direction of arrival of a non-perpendicular signal can be calculated, for example, from the delay of arrival at the different microphones. Conversely, appropriate delays may be added to the signals captured by the different microphones to make the signals aligned to one another prior to summing. This may emphasize the signals from one particular direction, and can therefore be used to form a beam or sensitivity pattern along the particular direction without physically moving the antennas. The beamforming process described above is known as delay-sum beamforming.

Figure 1B:
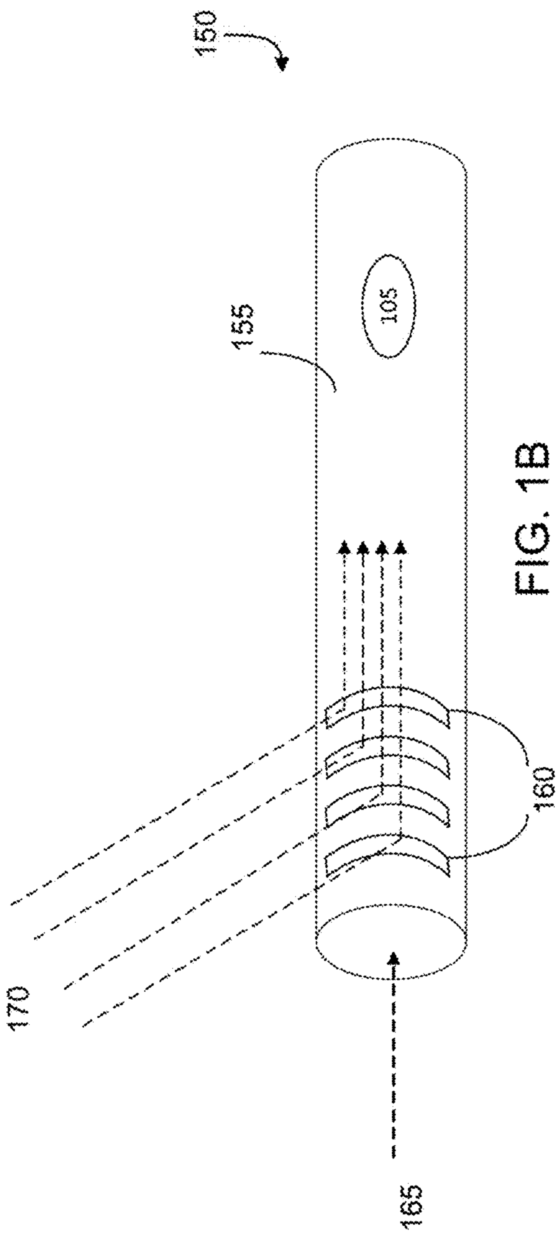
FIG. 1B is an example of a device that includes a microphone disposed within a slotted interference tube.

In some implementations, a directional audio capture device may also be realized using a single microphone together with a slotted interference tube. An example of such a device 150 is shown in FIG. 1B. The device 150 includes a single microphone 105 disposed within a tube 155 that includes multiple slots 160 that allow off-axis acoustic signals 170 to enter the tube 155. On-axis acoustic signals 165 enter the tube through the opening at one end of the tube 155. The desired on-axis acoustic signals 165 may propagate along the length of the tube to the microphone 105, while the unwanted off-axis acoustic signals 170 reaches the microphone 105 by entering the tube 155 through the slots 160 as shown in FIG. 1B. Because the off-axis acoustic signals 170 enter through the multiple slots 160, and the distances of the microphone from the different slots 160 are unequal, the off-axis acoustic signals 170 may arrive at the microphone with varying phase relationships that may partially cancel one another. Such destructive interference may cause at least a portion of the off-axis acoustic signals 170 to be attenuated relative to the on-axis acoustic signals 165, thereby yielding a sensitivity pattern that is more directional than what is possible using only the microphone 105. The tube 155 may be referred to as an interference tube, and the device 150 may be referred to as a shotgun (or rifle) microphone.

Nyquist criterion dictates that in order to reconstruct an audio signal from a set of spatial samples (e.g., with uniform sampling occurring along a given spatial dimension), the sampling period must be equal to less than half of the wavelength corresponding to the smallest wavelength (or highest frequency) present in the audio signal. If this criterion is not satisfied, different components of the reconstructed signal may become indistinguishable from (or aliases of) one another, causing the reconstructed audio signal to be potentially distorted due to the effect known as spatial aliasing. Higher the bandwidth of the audio intended to be captured without spatial aliasing, smaller the spacing required between microphones in the corresponding array. In devices and applications directed to speech capture only (corresponding, for example, to a bandwidth of about 4 KHz-8 KHz), the spacing between microphones is typically high enough for microphone arrays to be implemented on various devices. However, for high-fidelity applications, where audio over a much larger bandwidth (e.g., 20 KHz) is intended to be captured, the spacing between the microphones in an array becomes small (e.g., in the order of a fraction of a centimeter), thereby requiring a large number of microphones that may not be feasible to implement in many applications. For example, in recording high-fidelity audio for virtual reality (VR) applications, it may be desirable to capture audio not just over the frequency range corresponding to speech, but over the entire human audible range spanning approximately 20 KHz. The large number of microphones and/or the low spacing requirement may make it unfeasible for implementing a suitable microphone array for the purpose, for example, on small form-factor devices.

Figure 2:
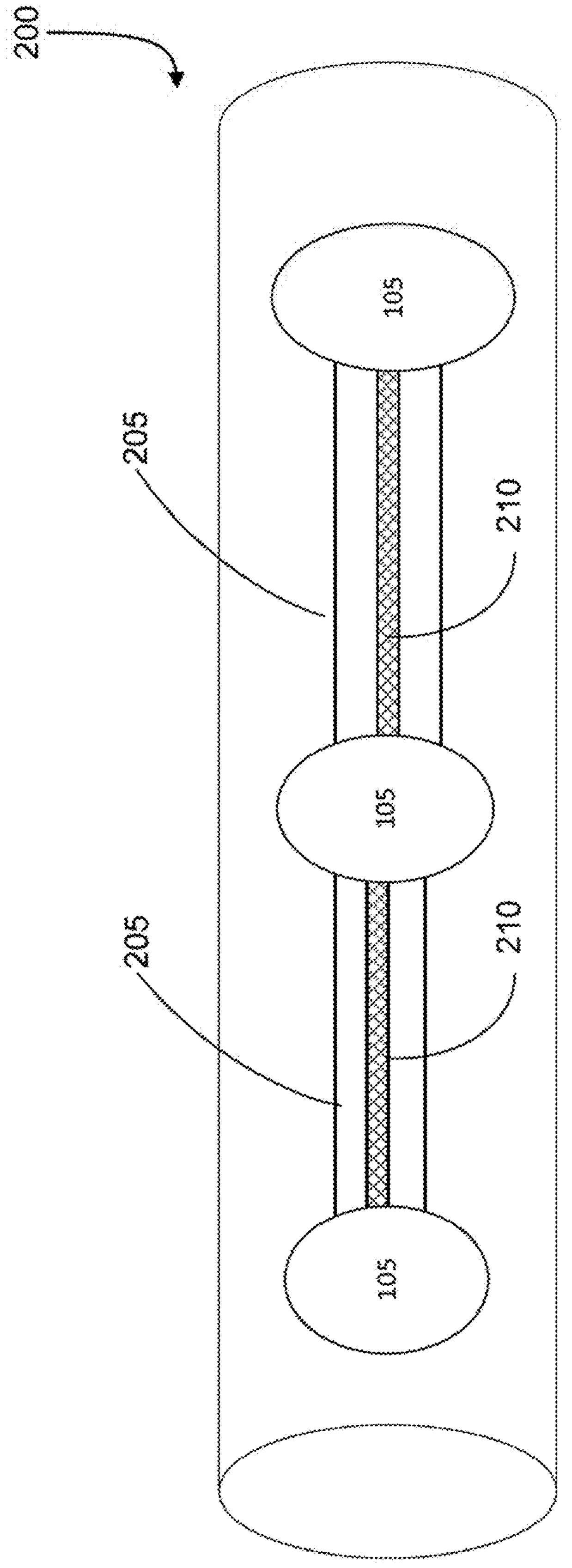
FIG. 2 is an example of a device having multiple microphones, with passive directional acoustic elements disposed between the microphones.
Figures 3A, 3B, 3C, 3D, 3E:
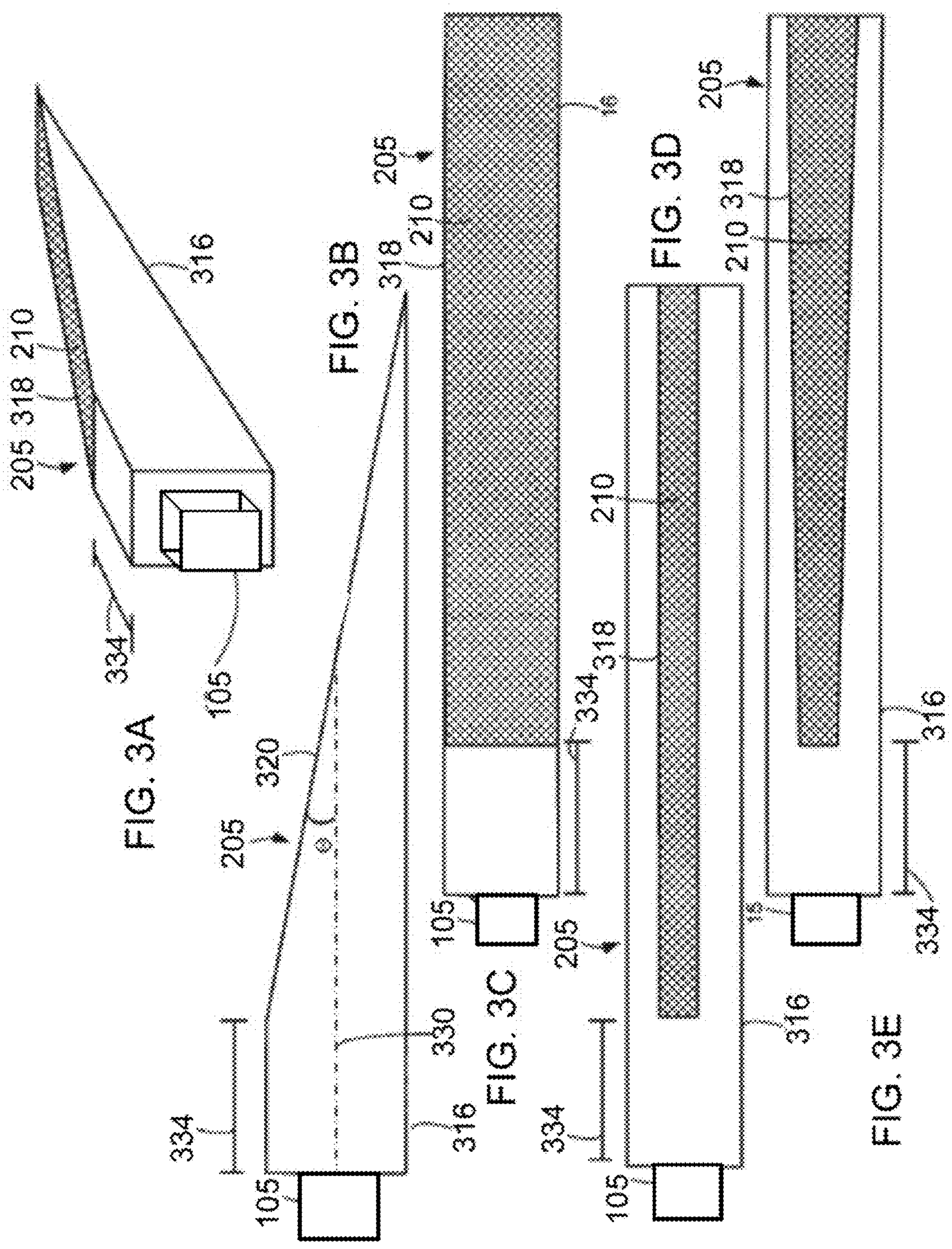
FIGS. 3A-3E are examples of passive directional acoustic elements usable in conjunction with technology described herein.

FIG. 2 shows an example of a device 200 that includes multiple microphones 105 separated by passive directional acoustic elements 205 disposed between the microphones 105. In some implementations, the passive directional acoustic elements 205 include a pipe or tubular structure having an elongated opening along at least a portion of the length of the pipe, and an acoustically resistive material 210 covering at least a portion of the elongated opening. The acoustically resistive material 210 can include, for example, wire mesh, sintered plastic, or fabric, such that acoustic signals enter the pipe through the acoustically resistive material and propagate along the pipe to one or more microphones 105. The wire mesh, sintered plastic or fabric includes multiple small openings or holes, through which acoustic signals enter the pipe. The passive directional acoustic elements 205 each therefore act as an array of closely spaced sensors or microphones, and may be used for capturing acoustic signals over a wide bandwidth such as 20 KHz.

Because the acoustically resistive material 210 acts as an array of microphones or sensors, and the arrival of an acoustic signal at two consecutive sensors are delayed by approximately d/co (where d is the distance between the holes and co is the speed of sound), the resultant array acts as a directional microphone in a manner similar to the shotgun microphone described above with reference to FIG. 1B. However, using only one or more passive directional acoustic elements 205 in conjunction with a single microphone may render the resulting audio capture device to be too directional for many applications. For example, the sensitivity pattern of such an audio capture device may be represented by a narrow beam along one particular direction only. While the device may capture audio over a wide bandwidth, the overly high directionality may be undesirable for applications such as VR, where the intent may be to capture acoustic signals from various different directions.

In some implementations, using passive directional acoustic elements 205 in conjunction with an array of microphones may allow for achieving a desired tradeoff between bandwidth and directionality. For example, a device that includes a microphone array with a passive directional acoustic element 205 disposed between one or more pairs of microphones (such as the device 200 shown in FIG. 2) may be used for achieving such a tradeoff. The passive directional acoustic elements 205 in the device can be used for capturing signals over a wide bandwidth, and the relatively limited number of microphone signals may be used for beamforming to obtain a target amount of directionality of the device.

Various types and forms of passive directional acoustic elements 205 may be used for the technology described herein. In some implementations, a passive directional acoustic element 205 may have a substantially uniform and cylindrical hollow cross-section. In some implementations, the passive directional acoustic element 205 may have a rectangular cross section, and shaped to reduce impedance mismatch between the interior and exterior of the pipe or tubular structure. In some implementations, this may prevent the formation of standing waves within the passive directional acoustic elements 205. Various views of examples of passive directional acoustic elements 205 with a rectangular cross section are shown in FIGS. 3A-3E. In some implementations, a passive directional acoustic element 205 can include an elongated opening 318 in a pipe 316. The opening 318 may be represented by the intersection of the pipe 316 with a plane 320 oriented at a non-zero, non-perpendicular angle θ relative to the axis 330 of the microphone connected to the element 205. The opening 318 may be formed, for example, by cutting the pipe 316 at an angle with a planar saw blade. The lengthwise opening 318 may be covered by the acoustically resistive material 210. In some implementations, the pipe 316 can be a 2.54 cm (1 inch) nominal diameter pvc pipe and acoustically resistive material 20 can be wire mesh Dutch twill weave 65×552 threads per cm (165×1400 threads per inch). Other suitable materials usable as the acoustically resistive material 210 can include, for example, woven and unwoven fabric, felt, paper, and sintered plastic sheets. In some implementations, the angle θ can be about 10°. In some implementations, due to the substantial absence of standing waves in a pipe, the length of the pipe can be less constrained as compared to a pipe that supports standing waves. For example, the length 334 of the section of pipe from the microphone 105 to the beginning of the slot 318 can be any convenient dimension configured in accordance with, for example, the geometry of the microphone array. Various other types of passive directional acoustic elements 205 may be used in implementing the technology described herein. Examples of such passive directional acoustic elements 205 are illustrated and described in U.S. Pat. Nos. 8,351,630, 8,358,798, and 8,447,055, the contents of which are incorporated herein by reference.

In some implementations, using an array of microphone in conjunction with passive directional acoustic elements 205 allows high-fidelity wideband audio capture systems to be implemented on small form-factor devices. Examples of such devices include personal acoustic devices, video capture devices such as VR cameras, teleconference microphones, or other audio-visual devices used for capturing high-fidelity wideband audio. In some implementations, in addition to the microphones and passive directional acoustic elements, a device can also include one or more acoustic transducers for generating audio signals and/or one or more processing devices configured to process, for example, signals captured or recorded using the microphones and passive directional acoustic elements.

Figure 4A:
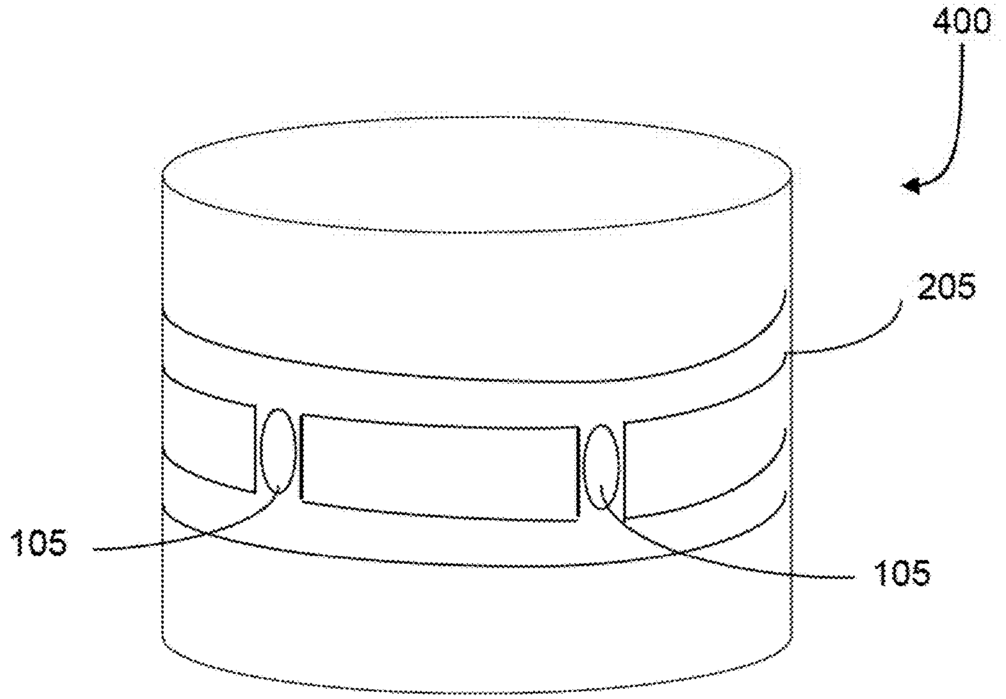
FIGS. 4A and 4B are examples of devices with microphones and passive directional acoustic elements disposed on a sidewall and top surface, respectively.
Figure 4B:
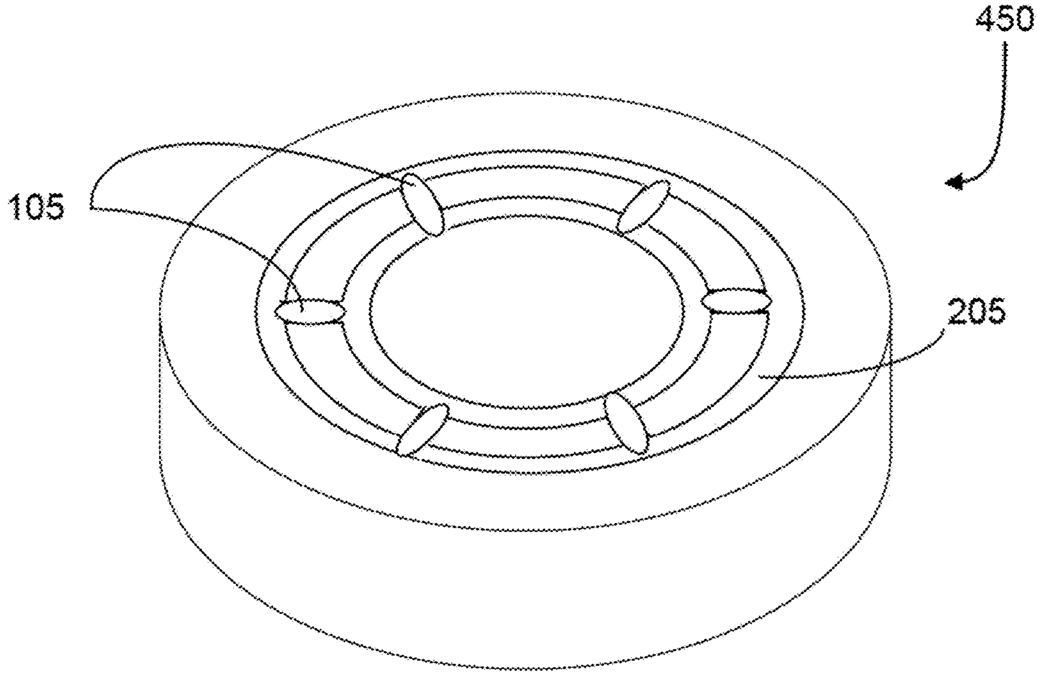

The technology described herein may be implemented on devices of various shapes and sizes. Examples of such devices are illustrated in FIGS. 4A and 4B. FIG. 4A shows an example of a substantially cylindrical device 400 in which microphones 105 and passive directional acoustic elements 205 are disposed on a curved sidewall of the device. The microphones may also be disposed around the periphery of a device (e.g., an acoustic device) with another shape (e.g., spherical, cubic, prismatic, or another arbitrary shape). FIG. 4B shows an example of a substantially cylindrical device 450 in which microphones 105 and passive directional acoustic elements 205 are disposed on a top surface of the device. In some implementations, the microphone array can be a non-linear array. For example, the microphones can be disposed in a non-linear arrangement such as in a circular or oval configuration as shown in FIGS. 4A and 4B. In such cases, the passive directional acoustic element 205 disposed between at least two of the multiple microphones has a curved shape, as also shown in the examples of FIGS. 4A and 4B. In some implementations, the microphone array can be a linear array such as a straight line array as shown in FIG. 2.

Figure 5:
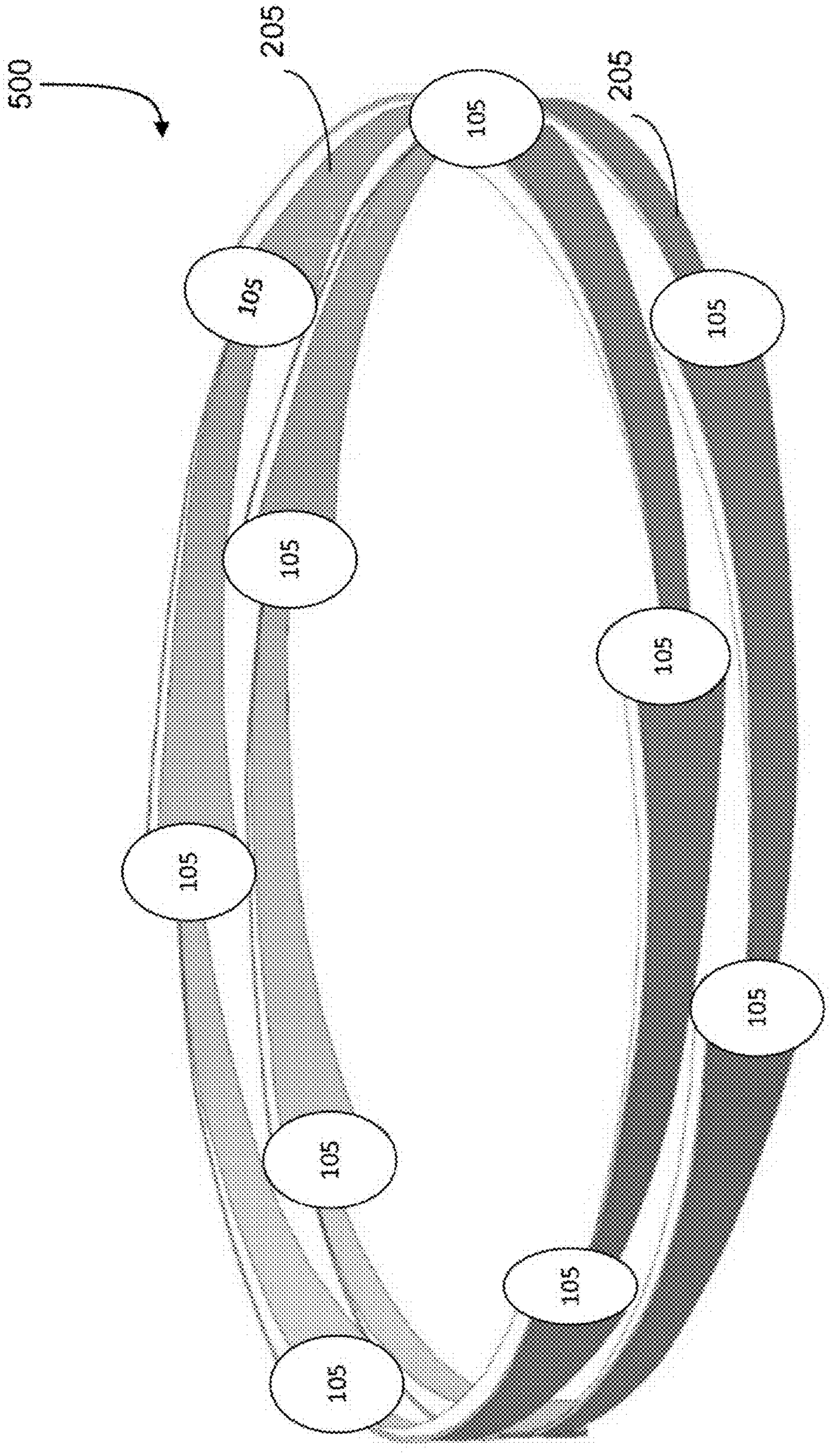
FIG. 5 shows an example configuration of microphones and passive directional acoustic elements usable with the technology described herein.

The examples of FIGS. 4A and 4B show devices that each have a single array of six microphones separated by passive directional acoustic elements. Larger or smaller number of microphones may also be used in the microphone arrays. In some implementations, multiple arrays of microphones may be disposed on a device. An example of such an arrangement 500 is shown in FIG. 5, which shows two non-linear arrays of microphones (with the microphones being separated by passive directional acoustic elements) disposed in a staggered and substantially parallel configuration. Such an arrangement can be used, for example, on the cylindrical sidewall of the device shown in FIG. 4A.

In some implementations, one or more structural characteristics of passive acoustic elements 205 disposed between microphones can be configured for capturing a target frequency range in accordance with a target beam pattern associated with the array. The target beam-pattern can be selected, for example, in accordance with a threshold or target amount of spatial aliasing. In some implementations, a length of a passive directional acoustic element can be determined based on a frequency above which the element effectively captures audio signals. In some cases, this can be determined as a fraction (e.g., substantially equal to ¼) of the corresponding wavelength. If six microphones are disposed on the sidewall of a cylindrical device of 8 cm diameter, the separation between two consecutive microphones (and hence the length of a curved passive directional acoustic element disposed between the microphones) is approximately 4 cm. The wavelength below which such a passive directional acoustic element may be found to be effective is substantially equal to 16 cm which corresponds to a frequency of about 2 KHz.

Figure 6A:
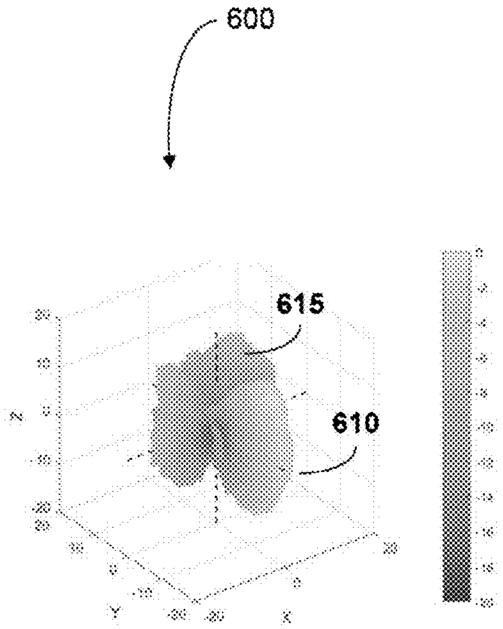
FIGS. 6A and 6B show sensitivity patterns of arrays without and with passive directional acoustic elements, respectively.
Figure 6B:
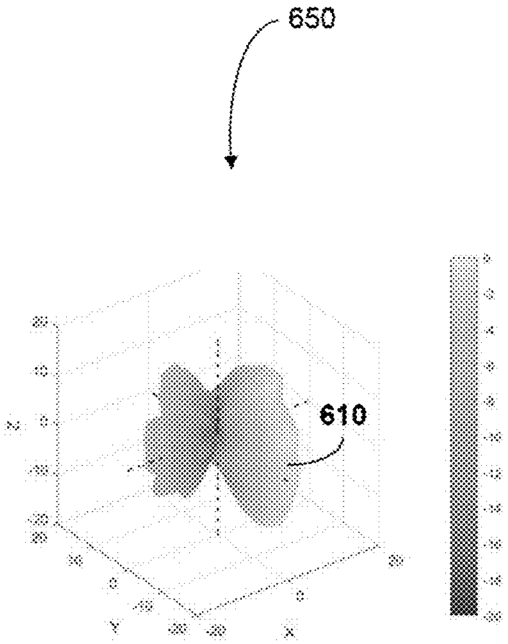

Therefore, a passive directional acoustic element of 4 cm may be used in capturing audio signals of frequencies 2 KHz or more. FIGS. 6A and 6B show sensitivity patterns 600 and 650 of arrays without and with passive directional acoustic elements, respectively. Specifically, FIG. 6A shows a sensitivity pattern 600 for an arrangement of six microphones disposed in a circular array, wherein the microphones do not have passive directional acoustic elements disposed in between. In FIG. 6A, the sensitivity pattern 600 includes a mainlobe 610 oriented substantially parallel to the Y axis at X=0, and a sidelobe 615 indicative of an effect of spatial aliasing. FIG. 6B shows a sensitivity pattern 650 for the same array, but with passive directional acoustic elements disposed between the microphones. In FIG. 6B, the improvement in spatial aliasing is evidenced by the reduction of the sidelobe, without any adverse effect on the mainlobe 610. FIGS. 6A and 6B therefore show how passive directional acoustic elements may be used for reducing spatial aliasing in a target sensitivity pattern.

Figure 7:
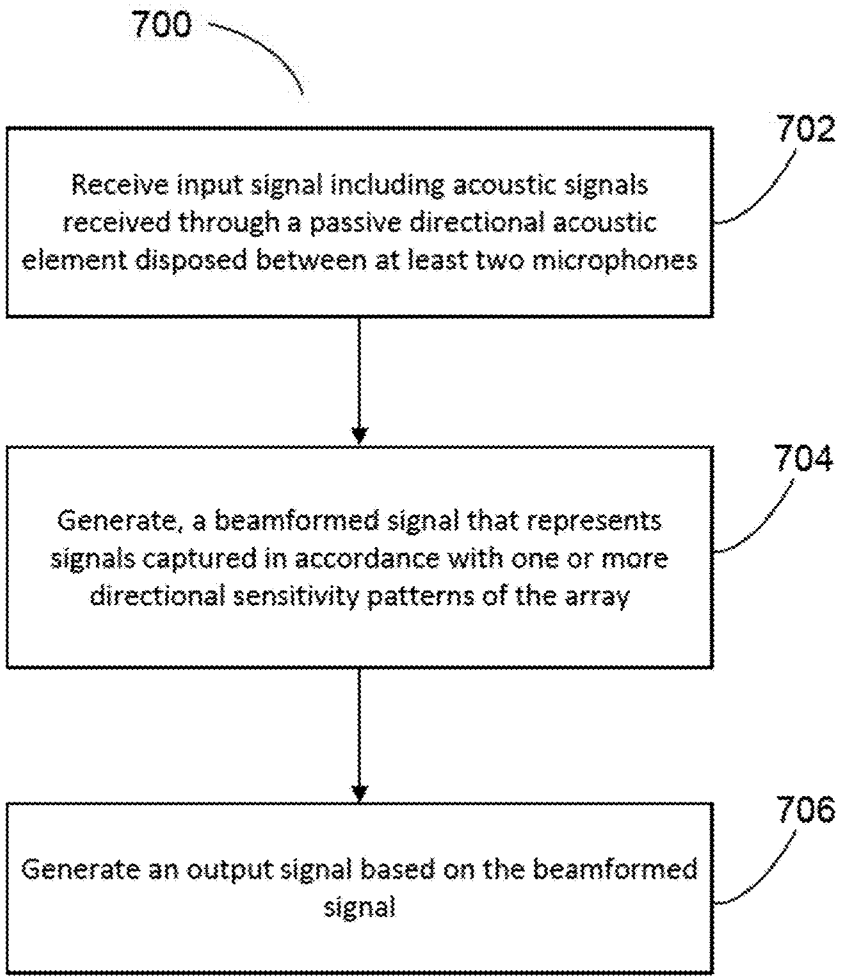
FIG. 7 is a flowchart of an example process for generating an output signal from an input signal captured using a microphone array with passive directional acoustic elements.

FIG. 7 is a flowchart of an example process 700 for generating an output signal from an input signal captured using a microphone array with passive directional acoustic elements. At least a portion of the process 700 may be performed using one or more processing devices of a device on which the microphone array with passive directional acoustic elements is disposed. In some implementations, a portion of the process 700 may be performed by one or more processing devices located at a remote location (e.g., a remote acoustic device that renders the audio captured by the microphone array with passive directional acoustic elements, or a remote cloud computing device).

Operations of the process 700 includes receiving an input signal from an array of multiple microphones, wherein the input signal includes acoustic signals received through a passive directional acoustic element disposed between at least two of the multiple microphones (702). The passive directional acoustic element can include a pipe having an elongated opening along at least a portion of the length of the pipe, and an acoustically resistive material covering at least a portion of the elongated opening. In some implementations, the passive directional acoustic element is substantially similar to those described above with reference to FIGS. 5A-5E, and/or those described in U.S. Pat. Nos. 8,351,630, 8,358,798, and U.S. Pat. No. 8,447,055, the contents of which are incorporated herein by reference. In some implementations, the passive directional acoustic element can be configured to capture the target frequency range in accordance with a target beam pattern associated with the array. The target beam-pattern can be selected in accordance with a threshold amount of spatial aliasing. In some cases, the target beam pattern may be selected from empirically determined beam patterns pre-stored in a non-transitory computer readable storage device. Structural parameters (length, cross-section, shape of opening, etc.) linked to the stored beam patterns may therefore be obtained and used for the passive directional acoustic elements.

Operations of the process 700 also includes generating a beamformed signal that represents signals captured by the array in accordance with one or more directional sensitivity patterns of the array (704). The beamformed signal can be generated, for example, using a delay-and-sum beamforming process such as one described above with reference to FIG. 1A. Operations of the process 700 can also include generating an output signal based on the beamformed signal (706). In some implementations, the output signal comprises signals in a target frequency range having bandwidth substantially equal to 20 KHz. The passive directional acoustic element can be configured to capture the target frequency range in accordance with a target beam pattern associated with the array. The target beam-pattern can be selected in accordance with a threshold amount of spatial aliasing.

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing all or part of the functions can be performed by one or more programmable processors executing one or more computer programs to perform the functions of the calibration process. All or part of the functions can be implemented as, special purpose logic circuitry, e.g., an FPGA and/or an ASIC (application-specific integrated circuit). In some implementations, at least a portion of the functions may also be executed on a floating point or fixed point digital signal processor (DSP) such as the Super Harvard Architecture Single-Chip Computer (SHARC) developed by Analog Devices Inc.

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

Other embodiments and applications not specifically described herein are also within the scope of the following claims. For example, the parallel feedforward compensation may be combined with a tunable digital filter in the feedback path. In some implementations, the feedback path can include a tunable digital filter as well as a parallel compensation scheme to attenuate generated control signal in a specific portion of the frequency range.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

What is claimed is:

1. An apparatus comprising:

an array of multiple microphones disposed on a surface of an acoustic device;

a passive directional acoustic element disposed between at least two of the multiple microphones, the at least two of the multiple microphones being substantially aligned along a longitudinal axis of the passive directional acoustic element, the passive directional acoustic element comprising:

a pipe having an elongated opening along at least a portion of the length of the pipe, and an acoustically resistive material covering at least a portion of the elongated opening, wherein one or more structural characteristics of the passive directional acoustic element is configured for capturing a target frequency range in accordance with a target beam-pattern associated with the array; and one or more processing devices configured to execute a beamforming process based on the signals captured by the array to generate a beamformed acoustic signal.

2. The apparatus of claim 1, wherein the array is a linear array.

3. The apparatus of claim 1, wherein the array is a non-linear array.

4. The apparatus of claim 1, wherein the multiple microphones are disposed around the periphery of an acoustic device.

5. The apparatus of claim 1, wherein the pipe has a substantially uniform hollow cross-section along the length of the pipe.

6. The apparatus of claim 1, wherein the acoustically resistive material comprises at least one of: wire mesh, sintered plastic, or fabric.

7. The apparatus of claim 1, wherein the array comprises six or more microphones separated by passive directional acoustic elements.

8. The apparatus of claim 1, wherein the array of multiple microphones is disposed along a substantially circular path, and the passive directional acoustic element disposed between at least two of the multiple microphones has a curved shape.

9. The apparatus of claim 1, wherein the array of multiple microphones is disposed on a top surface or sidewall of the apparatus.

10. The apparatus of claim 1, wherein the target beam-pattern is selected in accordance with a threshold amount of spatial aliasing.

11. The apparatus of claim 1, wherein the target frequency range has a bandwidth substantially equal to 20 KHz.

12. The apparatus of claim 1, wherein the surface comprises a top surface of the acoustic device.

13. The apparatus of claim 1, wherein the pipe includes an interior surface and an exterior surface, and the elongated opening is disposed such that a portion of an interior surface of the pipe is exposed to the environment through the elongated opening.

14. An acoustic device comprising:

one or more acoustic transducers;

an array of multiple microphones disposed on a surface of the acoustic device;

a passive directional acoustic element disposed between at least two of the multiple microphones, the at least two of the multiple microphones being substantially aligned along a longitudinal axis of the passive directional acoustic element, the passive directional acoustic element comprising:

a pipe having an elongated opening along at least a portion of the length of the pipe, and an acoustically resistive material covering at least a portion of the elongated opening, wherein one or more structural characteristics of the passive directional acoustic element is configured for capturing a target frequency range in accordance with a target beam-pattern associated with the array, the target beam-pattern being selected in accordance with a threshold amount of spatial aliasing; and one or more processing devices configured to process signals captured by the array.

15. The acoustic device of claim 14, wherein the one or more processing devices are configured to execute a beamforming process based on the signals captured by the array.

16. The acoustic device of claim 14, wherein the pipe has a substantially uniform hollow cross-section along the length of the pipe.

17. The acoustic device of claim 14, wherein the array of multiple microphones is disposed along a substantially circular path on a top surface or a sidewall of the device.

18. The acoustic device of claim 14, wherein the target frequency range has a bandwidth substantially equal to 20 KHz.

19. The acoustic device of claim 14, wherein the surface comprises a top surface of the acoustic device.

20. A method comprising:

receiving an input signal from an array of multiple microphones disposed on a surface of an acoustic device, wherein the input signal includes acoustic signals received through a passive directional acoustic element disposed between at least two of the multiple microphones, the at least two of the multiple microphones being substantially aligned along a longitudinal axis of the passive directional acoustic element, the passive directional acoustic element including:

a pipe having an elongated opening along at least a portion of the length of the pipe, and an acoustically resistive material covering at least a portion of the elongated opening;

generating, by one or more processing devices from the input signal, a beamformed signal that represents signals captured by the array in accordance with one or more directional sensitivity patterns of the array; and generating an acoustic output signal based on the beamformed signal.

21. The method of claim 20, wherein the output signal comprises signals in a target frequency range having bandwidth substantially equal to 20 KHz.

22. The method of claim 21, wherein the passive directional acoustic element is configured to capture the target frequency range in accordance with a target beam-pattern associated with the array, the target beam-pattern being selected in accordance with a threshold amount of spatial aliasing.

23. The method of claim 20, wherein the surface comprises a top surface of the acoustic device.

24. One or more machine-readable storage devices having encoded thereon computer readable instructions for causing one or more processing devices to perform operations comprising:

receiving an input signal from an array of multiple microphones disposed on a surface of an acoustic device, wherein the input signal includes acoustic signals received through a passive directional acoustic element disposed between at least two of the multiple microphones that are substantially aligned along a longitudinal axis of the passive directional acoustic element, the passive directional acoustic element including:

a pipe having an elongated opening along at least a portion of the length of the pipe, and an acoustically resistive material covering at least a portion of the elongated opening, generating, by one or more processing devices from the input signal, a beamformed signal that represents signals captured by the array in accordance with one or more directional sensitivity patterns of the array; and generating an acoustic output signal based on the beamformed signal.

25. The one or more machine-readable storage devices of claim 24, wherein one or more structural characteristics of the passive directional acoustic element are configured for capturing a target frequency range in accordance with a target beam-pattern associated with the array, the target beam-pattern being selected in accordance with a threshold amount of spatial aliasing.

* * * * *